(12) United States Patent
Sealfon

(10) Patent No.: US 10,278,618 B2
(45) Date of Patent: May 7, 2019

(54) METHOD OF SELECTING A NEEDLE FOR SUBCUTANEOUS THERAPY

(71) Applicant: REPRO-MED SYSTEMS, INC., Chester, NY (US)

(72) Inventor: Andrew L Sealfon, Monroe, NY (US)

( * ) Notice: Subject to any disclaimer, the term of this patent is extended or adjusted under 35 U.S.C. 154(b) by 275 days.

(21) Appl. No.: 14/914,247

(22) PCT Filed: Aug. 27, 2014

(86) PCT No.: PCT/US2014/052937
§ 371 (c)(1),
(2) Date: Feb. 24, 2016

(87) PCT Pub. No.: WO2015/031490
PCT Pub. Date: Mar. 5, 2015

(65) Prior Publication Data
US 2016/0213284 A1    Jul. 28, 2016

(51) Int. Cl.
| A61B 5/00 | (2006.01) |
| A61M 5/46 | (2006.01) |
| A61B 5/107 | (2006.01) |
| A61M 5/158 | (2006.01) |

(52) U.S. Cl.
CPC .......... *A61B 5/1075* (2013.01); *A61B 5/0053* (2013.01); *A61B 5/442* (2013.01); *A61B 5/443* (2013.01); *A61B 5/4872* (2013.01); *A61B 5/6849* (2013.01); *A61M 5/158* (2013.01); *A61M 5/46* (2013.01)

(58) Field of Classification Search
CPC .... A61B 5/1075; A61B 5/4872; A61M 5/158; A61M 5/46
See application file for complete search history.

(56) References Cited

U.S. PATENT DOCUMENTS

| 4,233,743 A | 11/1980 | Flick |
| 4,235,234 A * | 11/1980 | Whitney ................. A61M 5/46 604/117 |
| 4,321,752 A * | 3/1982 | Kaufman ............. A61B 5/1075 33/512 |
| D268,245 S | 3/1983 | Makino et al. |
| 4,675,006 A * | 6/1987 | Hrushesky ............ A61M 25/02 128/DIG. 26 |
| 5,156,161 A | 10/1992 | Lollar |
| 9,974,463 B2 * | 5/2018 | Rutkove ................. A61B 5/053 |
| 2006/0058736 A1 * | 3/2006 | Alchas ................. A61K 39/145 604/117 |

(Continued)

FOREIGN PATENT DOCUMENTS

| GB | 2 349 473 A | 11/2000 |
| WO | WO 02/060325 | 8/2002 |

OTHER PUBLICATIONS

Michelle DiGregorio, High-Flo(TM) Confirmed as Safety Sets, RMD Medical Products (Year: 2012).*

(Continued)

*Primary Examiner* — Sean P Dougherty
(74) *Attorney, Agent, or Firm* — Daniel W. Roberts; Law Offices of Daniel W. Roberts, LLC

(57) ABSTRACT

The invention relates to methods of selecting needles with an injection length suited for administration of a therapeutic agent in the subcutis at a body location.

24 Claims, 1 Drawing Sheet

(56) References Cited

U.S. PATENT DOCUMENTS

| | | | | |
|---|---|---|---|---|
| 2007/0259806 | A1* | 11/2007 | Hastings | C07K 14/8132 424/139.1 |
| 2010/0130985 | A1 | 5/2010 | Tanaka | |
| 2011/0054355 | A1* | 3/2011 | Hunter | A61B 5/0053 600/587 |
| 2012/0065615 | A1* | 3/2012 | Boyd | A61M 5/30 604/500 |
| 2012/0101475 | A1* | 4/2012 | Wilmot | A61M 5/2033 604/506 |
| 2012/0157854 | A1* | 6/2012 | Kurrus | A61M 25/06 600/461 |
| 2013/0172704 | A1* | 7/2013 | Kuenstner | A61B 5/145 600/347 |
| 2014/0221837 | A1* | 8/2014 | Park | A61B 8/0858 600/449 |
| 2014/0221934 | A1* | 8/2014 | Janvier | A61M 5/3129 604/187 |
| 2015/0231338 | A1* | 8/2015 | Alchas | A61M 5/46 604/117 |
| 2016/0008556 | A1* | 1/2016 | Baym | A61M 5/427 604/506 |
| 2017/0259009 | A1* | 9/2017 | Sjokvist | A61M 5/3204 |
| 2018/0028753 | A1* | 2/2018 | Wilmot | A61M 5/2033 |

OTHER PUBLICATIONS

Kang Hee Sim, et al., The Appropriateness of the Length of Insulin Needles Based on Determination of Skin and Subcutaneous Fat Thickness in the Abdomen and Upper Arm in Patients with Type 2 Diabetes, pp. 120-133, Diabetes Metab J 2014;38:120-133, pISSN 2233-6079 • eISSN 2233-6087 (Year: 2014).*

Extended European Search Report for Application 14839103.0-1657 / 3038680 PCT/US2014/052937 Dated Mar. 7, 2017 (Mar. 7, 2017).

Sasaki et al: "Clinical parameters for predicting efficacy and safety with nonablative monopolar radiofrequency treatments to the forehead, face, and heck", Aesthetic Surgery Journal, Mosby-Year Book, St. Louis, Mo. US, vol. 27, No. 4, Aug. 6, 2007 (Aug. 6, 2007), pp. 376-387, XP022205038, ISSN: 1090-820X, DOI: 10.1016/J.ASJ.2007.05.007.

A.D. Martin et al: "Effects of skin thickness and skinfold compressibility on skinfold thickness measurement", American Journal of Human Biology, Vo. 4, No. 4, Jan. 1, 1992 (Jan. 1, 1992), pp. 453-460, XP055349801, US ISSN: 1042-0533, DOI: 10.1002/ajhb.1310040404.

PCT International Search Report for International Application PCT/US2014/052937, search report dated Aug. 27, 2014 (Aug. 27, 2014).

* cited by examiner

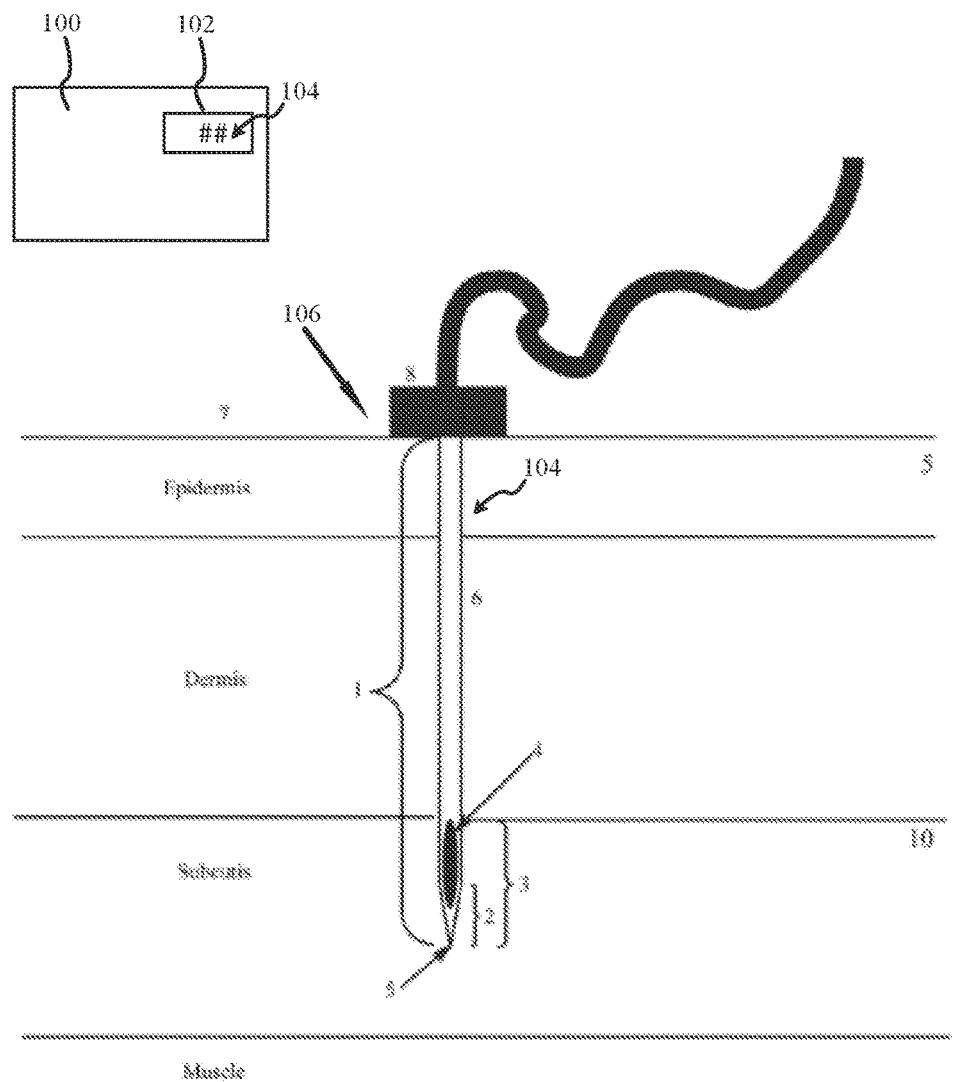

METHOD OF SELECTING A NEEDLE FOR SUBCUTANEOUS THERAPY

FIELD OF THE INVENTION

The invention relates to methods of selecting a needle with an injection length suited for administration of a therapeutic agent in the subcutis at a body location.

BACKGROUND OF THE INVENTION

The subcutaneous route is one of the most versatile routes of administration in that it can be used for both short term and very long term therapies. Additional benefits of subcutaneous administration include favorable bioavailability and pharmacokinetic properties and ease of delivery independent of the consciousness or rationality of the patient. While the subcutaneous tissue is an important target of drug delivery, it can be difficult to determine the boundaries of the subcutis between the dermal layers and underlying muscle tissue. For many medications, accidental administration within the cutis or the muscle tissue can lead to side effects, incorrect dosage or leakage of the medication from the injection site.

For example, insulin accidentally injected into the muscle tissue will be absorbed more rapidly than if injected into the subcutaneous tissue and this is potentially dangerous as it may cause low levels of blood glucose. Other therapies, such as immunoglobulins, can irritate mast cells if injected into the dermal layers. For these therapies, clearing the dermal layers is important to avoid reactions which can include swelling, redness, itching, pain, and in some cases, the drug leaking out of the injection sites due to the swelling surrounding the area.

The injection into the subcutis can be controlled by the length of the needle used for the injection or infusion. However, it is often difficult to know the required length of needle needed to clear the cutis given the variability in body fat compositions at different locations in the body. Skin irregularities such as scar tissue add even more complexity to the determination of cutis depth.

Some groups have looked at methods of localizing insulin injections in the subcutis by determining muscle depth. Using ultrasonic means, the maximum allowable penetration length of a needle may be determined to avoid injection of insulin into the muscle and the accompanying negative side effects.

There remains a need for a reliable, accurate and inexpensive way to determine depth of the cutis to avoid injection of a potential irritant, such as an immunoglobulin, into the dermal tissue.

SUMMARY OF THE INVENTION

The invention provides a method for selecting a needle with an injection length for subcutaneous injection of a therapeutic agent at a body location, comprising measuring body fat at the body location and selecting a needle with an injection length suited to position the anterior opening of the needle within the subcutis at the body location. The method may further include the step of correlating the body fat measurement with a depth of body fat at the body location.

The body fat at a body location may be measured with a skinfold caliper. Examples of skinfold calipers include the Accu-Measure® Fitness 3000 Personal Body Fat Tester, Baseline Skinfold Caliper, Slim Guide Skinfold Caliper, and AccuFitness FatTrack II Digital Body Fat Caliper. In particular, the skinfold caliper is the Accu-Measure® Fitness 3000 Personal Body Fat Tester.

The body location may be selected from the abdomen, thigh, arm, such as the back of the arm, and hip, such as the back of the hip. The body fat measurement may include an average of two or more measurements at a body location.

The injection length of the needle may be the length of needle from the tip to the posterior end of the shaft or from the tip to a fixed point on the shaft. The fixed point may be a block to prevent injection past the block. The fixed point may be a bend in the needle to prevent injection past the bend, such as a bend of the needle at about a 90 degree angle.

The injection length of the needle may be selected from between about 3 mm and about 20 mm. For example, the injection length of the needle is selected from about 4 mm, about 6 mm, about 9 mm, about 12 mm and about 14 mm. The injection length of the needle may be selected from about 0.1 mm to about 5 mm greater than the depth of body fat at the body location. In particular, the injection length may be selected from about 1 mm to about 3 mm greater than the depth of body fat at a body location. In certain embodiments, the needle is a RMS High-Flo® needle.

The invention includes the method for selecting a needle with an injection length for subcutaneous injection of a therapeutic agent at a body location, comprising measuring body fat at a body location with a skinfold caliper and selecting a needle with an injection length suited to position the anterior opening of the needle within the subcutis at the body location.

The invention includes a method for selecting a needle with an injection length for subcutaneous injection of a therapeutic agent at a body location, comprising measuring body fat at a body location, correlating the body fat measurement with a depth of body fat at the body location, and selecting a needle length suitable to position the anterior opening of the needle within the subcutis at the body location.

The invention further includes a method for subcutaneous injection of a therapeutic agent at a body location, comprising measuring body fat at a body location, selecting a needle with an injection length suited to position the anterior opening of the needle within the subcutis at the body location, inserting the needle at an angle perpendicular or approximately perpendicular to the skin surface to the extent that the anterior opening of the needle is within the subcutis at the body location, and injecting the therapeutic agent.

In other aspects, the invention provides a skinfold caliper for selecting a needle with an injection length suited for positioning the anterior opening of the needle in the subcutis, wherein the skinfold caliper measures the width of a skin fold and outputs a suitable injection length or injection length range for a needle. The output of the skinfold caliper may be selected from digital or analog. The needle may be inserted at an angle perpendicular or approximately perpendicular to the skin surface.

BRIEF DESCRIPTION OF THE FIGURES

FIG. 1 depicts a needle within the tissue layers of the skin and the positioning of the anterior opening of a needle in the subcutis.

DESCRIPTION OF THE INVENTION

The invention provides a method of selecting a needle with an injection length for subcutaneous injection of a therapeutic agent at a body location. To select the appropriate length needle the body fat at the body location is measured. The measurement of body fat at the body location is used to select a needle with an injection length suited to position the anterior opening of the needle within the subcutis at the body location.

The measurement of body fat at a body location generally refers to a measurement of the depth of body fat and dermal tissue in the dermal layers. The cutis or cutaneous portion of the skin includes the epidermis and dermis while the subcutis or subcutaneous tissue is located between the cutis and muscle tissue. The amount of body fat in the dermal layers may vary dramatically from one individual to another and at one location on the body to another location on the same individual. For example, the depth of body fat at a location in the abdomen may vary by multiple millimeters relative to the depth of body fat measured in the thigh. To further illustrate the variability, the depth of body fat at one location in the abdomen may vary relative to another position of the abdomen of the same individual. In some instances there will be no body fat in the dermal layers and the measurement of body fat will afford the depth of the dermal tissue.

One way to measure the amount of body fat at a body location is to use a skinfold caliper. According to the invention, the body fat measured by a skinfold caliper at a body location may be used to select a needle for subcutaneous injection. The skinfold caliper measures a fold of the skin tissue which is greater than the depth of fat in the cutis at a body location. The invention provides a correlation between the skin fold measurement at a body location and depth of body fat at that location. The depth of body fat is the depth of body fat and dermal tissue in the dermal layers. In cases where there is no body fat in the dermal layers at a body location, the depth of body fat is the depth of the dermal layers. The depth of body fat determined using a skinfold caliper may then be used to select a needle appropriate for administration of a therapeutic agent into the subcutis. In certain embodiments, the caliper measurement of body fat is used to select a needle length without intermediate correlation to depth of body fat. For example, a table provides a correlation between skin fold measurements and suitable needle length at the body location. Exemplary skinfold calipers include the Accu-Measure® Fitness 3000 Personal Body Fat Tester, Baseline Skinfold Caliper, Slim Guide Skinfold Caliper, and AccuFitness FatTrack II Digital Body Fat Caliper. In preferred embodiments, the skinfold caliper is the Accu-Measure® Fitness 3000 Personal Body Fat Tester.

The skinfold caliper used in methods of the invention is generally operated in a fashion consistent with its use in the field of body fat measurement. Measurement technique may vary slightly by body location, by operator or by other considerations. In general, a fold of skin is gathered between the thumb and forefinger of one hand. In some measurements, the skin fold may be slightly pulled away from the underlying muscle. Holding the calipers in the other hand, jaws of the caliper are positioned to clasp the skin fold about ¼" from the fingers holding the fold. The trigger of the caliper is released so that the force of the jaws is on the skin fold. The skin fold may be concurrently held with the thumb and forefinger during the release of the caliper trigger. Once the caliper jaws are clasped around the fold of skin, the measurement may be taken immediately or the measurement may be taken after passage of a short period of time, e.g., 10-20 seconds. A delay in measurement may allow the fold of skin to settle or adjust in the clasp of the calipers which may lead to a more accurate reading. Some skinfold calipers require that the measurement be read while the caliper is clasped around the skin fold. Other more preferable skinfold calipers allow for reading of the measurement following removal of the calipers from the skin fold. The procedure for measuring body fat at a body location may be repeated multiple times at a body location. In certain embodiments, the measurement is taken multiple times, such as two, three four or five times, and the measurements averaged.

In certain embodiments, the invention provides a method of correlating body fat at a body location with an appropriate length needle for subcutaneous injection. For example, the invention provides a conversion factor or table for converting a body fat measurement at a body location and thereby selecting an appropriate length needle for subcutaneous injection. In other embodiments, the invention provides a method of correlating body fat at a body location with a body fat depth which may then be correlated with an appropriate length needle for subcutaneous injection.

In other embodiments, a skinfold caliper is graduated with needle lengths or has a digital output of a needle length, such that no correlation or table is required by the user to convert a body fat measurement to an appropriate needle length. conceptualized as In such embodiments, a body fat measurement may be taken with a caliper at a body location but the output on the caliper is a needle length rather than the skin fold width generally read from the skinfold caliper. For example, the skinfold caliper clasps the skin fold at a location in the abdomen and the measurement on the caliper reads 9 mm needle, such that a 9 mm needle is a suitable needle length to try for subcutaneous injection at that body location. Moreover, as shown in FIG. 1, conceptualized caliper 100, has an output display 102 to inform the user of the determined needle 104, appropriate for body location 106.

In certain embodiments, the method of the invention further comprises the step of inserting the needle through the dermal tissue into the subcutis. For example, the method comprises measuring the body fat at a body location, selecting a needle with a length suitable to position the needle in the subcutis and inserting the selected needle into the subcutis. The needle may be inserted perpendicular or approximately perpendicular to the surface of the skin. For example, the needle may be inserted at about a 90 degree angle relative to the skin surface. In other embodiments, the needle is injected at an angle relative to the skin surface such as about a 10 degree angle or less to the skin surface, about a 20 degree angle or less to the skin surface, about a 30 degree angle or less to the skin surface, about a 40 degree angle or less to the skin surface, about a 50 degree angle or less to the skin surface, about a 60 degree angle or less to the skin surface, about a 70 degree angle or less to the skin surface, or about a 80 degree angle or less to the skin surface. In certain embodiments, the full injection length is inserted into the skin. In other embodiments, a portion of the injection length is inserted into the skin. In certain embodiments, the anterior opening of the needle is below the cutis or substantially within the subcutis tissue. The method may further comprise injecting or infusing a therapeutic agent into the subcutis.

The methods of the invention may be practiced at any location on the body in which subcutaneous injection is desired. In certain embodiments, the body location is selected from the abdomen, thigh, arm, such as the back of the arm, and the hip, such as the back of the hip. Body fat at different locations on the body may vary significantly such that measurement at one body location provides information on depth of fat and needle length specific to that measured location. For example, the body fat measurement on the back of the upper arm may only provide guidance for selecting a needle length at that location on the body. In other embodiments, the body fat measurement at one body location may provide guidance for needle length selection at other locations on the body. For example, body fat measurement on the back of the right arm may be sufficient to determine needle length for the analogous position on the back of the left arm.

The total length of a needle from the tip to the posterior end of the shaft, may not correspond to the injection length of a needle. For example, a needle may be bent at a 90 angle such that only the portion anterior to the angle is suited for injection into the body. In other embodiments, the needle has a block on the shaft of the needle, such that injection cannot occur beyond the block in the needle. For example, a block located around the shaft of the needle stops the needle from injection deeper into the body once the disk contacts the skin surface. The injection length of a needle 1 is measured from the anterior tip of the needle to the furthest injectable point on the shaft 6 of the needle (FIG. 1). For example, the injection length of the needle may be measured from tip of the needle to posterior end of the shaft. In other embodiments, the injection length is the length of the needle from the tip to a fixed point on the shaft such as a bend in the needle or a block 8 in the needle that prevents further injection beyond the block or the bend (FIG. 1).

In preferred embodiments, the needle is injected at an angle perpendicular or approximately perpendicular to the surface of the skin. That is, the shaft of the needle enters and traverses the skin layers at the shortest pathway to the subcutis at that position. In other embodiments, the shaft of the needle may traverse the skin layers at an angled trajectory.

In preferred embodiments, the full extent of the injection length is injected into the body location. For example, for a needle with an injection length of 9 mm, the full 9 mm of the needle is injected perpendicularly or approximately perpendicularly through the cutis and into the subcutis. In other embodiments, a portion of the injection length is injected into the body location. For example, for a needle with an injection length of 9 mm, 8 mm of the needle is injected perpendicularly or approximately perpendicularly through the cutis and into the subcutis and 1 mm of the injection length remains exterior to the body.

The anterior opening of a needle 4 is generally positioned distal to the tip 5 of a needle (FIG. 1). In preferred embodiments, a needle is selected with an injection length 1 such that the needle is suited to position the anterior opening of the needle 4 below the cutis and within the subcutis of the body location 3 (FIG. 1). A needle with an injection length suited to position the anterior opening 4 below the cutis may be longer than the distance required to clear the cutis and enter the subcutis (FIG. 1). For example, the injection length suited to position the anterior opening of the needle below the cutis is 10 mm and the injection length of the needle is 11 mm. For such an example, the full injection length may be inserted perpendicularly or approximately perpendicularly to the skin surface 7 to a point at which anterior opening resides further within the subcutis and closer to the muscle or alternatively 1 mm of the needle may remain exterior to the body (FIG. 1).

In other embodiments, a needle is selected with an injection length suited to position the anterior opening of the needle substantially within the subcutis. Substantially within the subcutis includes, for example, when a portion of the anterior opening, such as about 5% or less, about 10% or less, about 20% or less, or about 30% or less of the opening, is positioned in the cutis.

In certain embodiments, the injection length of the needle is selected from between about 3 mm and about 20 mm. In particular, the injection length is selected from about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.5 mm, and about 18 mm. For example, the injection length is selected from about 4 mm, about 4.5 mm, about 6 mm, about 6.5 mm, about 9 mm, about 9.5 mm, about 12 mm, about 12.5 mm, about 14 mm and about 14.5 mm. In certain embodiments, the needle is a RMS High-Flo® needle. For certain needles it should be noted that the marketed needle length excludes the length of the tip 2 (FIG. 1). For example, the needle is marketed as a 9 mm needle but the injection length is 9.5 mm.

The method of the invention provides a correlation between measurement of body fat and depth of body fat in the cutis. A correlation is as follows:

$$\text{Depth of body fat} = \frac{SF}{2} + f(p) + f(SF) * SF$$

wherein SF=skin fold measurement at a body location, f(p)=adjustment for pressure of compression, and F(SF)*SF=factor for size adjustment. SF may be equal to a single skinfold measurement or SF may be the average of two or more measurements at a body location. The variable f(p) is an adjustment factor for tissue compression that may vary from one body location to another. For example, the compression of tissue at a location on the abdomen may be greater than the compression at the thigh due to differences in the tissue density resulting in the need for a larger adjustment for the abdomen. In certain embodiments, the f(p) may be selected from about 0.1 to about 4 mm, such as about 1 to about 3 mm. In certain embodiments, the f(p) may be zero.

F(SF)*SF is an adjustment factor for inaccuracies that may exist for large skinfold measurements. F(SF) may be from about 0.01 to about 0.5, such as about 0.05 to about 0.3. In certain embodiments, the F(SF) may be zero.

Depth of body fat may be correlated with the injection length of a needle. The injection length of the needle may be selected from about 0.1 mm to about 5 mm greater than the depth of body fat at the body location, such as from about 1.0 mm to about 3.0 mm greater than the depth of body fat. In certain embodiments, the injection length of the needle may be selected from between about 0.1 to about 1 mm greater than depth of body fat, about 1 mm to about 2 mm greater than the depth of body fat, about 2 mm to about 3 mm greater than the depth of body fat, about 3 mm to about 4 mm greater than the depth of body fat or about 4 mm to about 5 mm greater than the depth of body fat.

In certain embodiments, subcutaneous injection of a therapeutic agent includes subcutaneous infusion of a therapeutic agent. Subcutaneous infusion or continuous subcutaneous infusion is a way to deliver one or more therapeutic agents over extended periods of time and is particularly useful for palliative care. Subcutaneous infusion is used in both the inpatient and outpatient settings, for example, for relief of malignant and non-malignant disease.

The therapeutic agent of the method may be selected from any therapeutic agent suitable for subcutaneous administration. Exemplary therapies for subcutaneous administration include isotonic fluid replacement, immunizations, immunoglobulins, iron chelating treatment, insulin, heparin, hormones and growth factors, cytotoxic chemotherapy, sedation and narcotic drugs, and opioids. In particular, the therapeutic agent is an immunoglobulin.

The invention further comprises a method for subcutaneous injection or infusion of a therapeutic agent at a body location, comprising measuring body fat at a body location, selecting a needle with an injection length suited to position the anterior opening of the needle within the subcutis at the body location, inserting the needle at an angle approximately perpendicular to the skin surface to the extent that the anterior opening of the needle is within the subcutis at the body location, and injecting or infusing the therapeutic agent. In certain embodiments, the injection or infusion is administered by a healthcare professional such as a nurse, nurse practitioner or doctor; self-administered; or administered by a third party such as a relative.

Another aspect of the invention is a skinfold caliper for selecting a needle with an injection length suited for positioning the anterior opening of the needle in the subcutis, wherein the skinfold caliper measures the width of a skin fold and outputs a suitable injection length or injection length range for a needle. The output, as used in reference to the skinfold caliper, is the measurement read from the caliper. The output of the skinfold caliper may be digital, for example, the caliper may have a digital screen that reads a suitable needle length upon measuring the width of a skin fold. The output of the skinfold caliper may be analog, for example, the scale of the caliper is graduated with needle length measurements. For example, the graduations on the caliper are needle lengths of 9 mm, 10 mm, 11 mm, etc, which are suitable needle lengths to try based upon the width of the skin fold at the body location. In certain embodiments, the needle is inserted into the skin at an angle perpendicular or approximately perpendicular to the skin surface.

The invention further comprises a skinfold caliper for selecting a needle with an injection length suited for positioning the anterior opening of the needle in the subcutis, wherein the skinfold caliper measures the width of a skin fold and outputs the depth of body fat at the body location. The output of the skinfold caliper may be digital or analog. The output from the caliper may be used to select a needle with an injection length suited for positioning the anterior opening of a needle in the subcutis. For example, the output of the skin fold measurement may be 10 mm, indicating that 11 mm is a suitable injection length to try to clear the cutis.

The skinfold caliper of the invention may be any caliper used in the field of measuring body fat, wherein the improvement comprises an output of body fat depth, rather than skin fold width, at a body location or a suitable needle length at a body location for positioning the anterior opening of a needle in the subcutis at the body position. The output of the skinfold caliper may be a digital output or it may be an analog output.

The present invention provides among other things methods of selecting needles with an injection length suited for subcutaneous administration of a therapeutic agent. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

What is claimed is:

1. A method for selecting a needle with an injection length for subcutaneous injection of a therapeutic agent into subcutis at a body location, comprising:
   measuring body fat at the body location with a skinfold caliper, the skinfold caliper determining the injection length of a needle suited to position an anterior opening of the needle within the subcutis at the body location, based on a correlation between skin fold measurements and suitable needle length for injection into the body, the skinfold caliper outputting the determined injection length.

2. The method of claim 1, further comprising correlating the body fat measurement with a depth of body fat at the body location.

3. The method of claim 2, wherein the skinfold caliper is selected from Accu-Measure® Fitness 3000 Personal Body Fat Tester, Baseline Skinfold Caliper, Slim Guide Skinfold Caliper, and AccuFitness FatTrack II Digital Body Fat Caliper.

4. The method of claim 2, wherein injection length is selected from about 0.1 mm to about 5 mm greater than the depth of body fat at the body location.

5. The method of claim 4, wherein the injection length of the needle is selected from about 1 mm to about 3 mm greater than the depth of body fat at the body location.

6. The method of claim 1, wherein the body location is selected from the abdomen, thigh, arm and hip.

7. The method of claim 1, wherein the needle has a shaft, a tip and a posterior end of the shaft, the injection length is the length of the needle from the tip to the posterior end of the shaft.

8. The method of claim 1, wherein the needle has a shaft, a tip and a posterior end of the shaft, the injection length is the length of the needle from the tip to a fixed point on the shaft.

9. The method of claim 8, wherein the fixed point comprises a block to prevent injection into the body beyond the block.

10. The method of claim 8, wherein the fixed point comprises a bend in the needle to prevent injection beyond the bend.

11. The method of claim 10, wherein the bend in the needle is at an angle of about 90 degrees.

12. The method of claim 1, wherein the injection length of the needle is selected from between about 3 mm and about 20 mm.

13. The method of claim 12, wherein the injection length is selected from about 4 mm, about 6 mm, about 9 mm, about 12 mm and about 14 mm.

14. The method of claim 1, wherein the needle is a RMS High-Flo® needle.

15. The method of claim 1, wherein the body fat measurement comprises an average of two or more measurements of body fat at a body location.

16. The method of claim 1, wherein the therapeutic agent is selected from isotonic fluid replacement, immunizations, immunoglobulins, iron chelating treatment, insulin, heparin, hormones and growth factors, cytotoxic chemotherapy, sedation, narcotic agents and opioids.

17. The method of claim 16, wherein the therapeutic agent is an immunoglobulin.

18. The method of claim 1, wherein the measurement of body fat is determined as $$(SF/2)*f(p)+f(SF)*SF,$$

wherein, SF is a skinfold measurement at a body location, (SF/2) being half the skinfold, f(p) is an adjustment for the pressure of compression during the measuring and is selected from a first range of about 0.1 to about 4 mm, and f(SF)*SF is an adjustment factor the the skinfold measurement, where f(SF) is selected from a second range of about 0.01 to about 0.5.

19. A method for selecting a needle with an injection length for subcutaneous injection of a therapeutic agent at a body location, comprising:
   measuring body fat at a body location with a skinfold caliper, the skinfold caliper providing a measurement correlated to a needle injection length to position an anterior opening of the needle within the subcutis at the body location, the skinfold caliper outputting the needle injection length.

20. The method of claim 19, wherein the needle has a shaft, a tip and a posterior end of the shaft, the injection length is the length of the needle from the tip to the posterior end of the shaft.

21. The method of claim 19, wherein the needle has a shaft, a tip and a posterior end of the shaft, the injection length is the length of the needle from the tip to a fixed point on the shaft.

22. The method of claim 21, wherein the fixed point comprises a block to prevent injection into the body beyond the block.

23. The method of claim 21, wherein the fixed point comprises a bend in the needle to prevent injection beyond the bend.

24. A method for selecting a needle with an injection length for subcutaneous injection of a therapeutic agent at a body location, comprising:
   measuring body fat (SF) at the body location with a skin fold caliper,
   determining a depth of body fat bused on the body fat measured at the body location, and
   based on the determined depth of body fat, selecting a needle with an injection length suited to position an anterior opening of the needle within the subcutis at the body location;
   wherein in that the depth of body fat is determined as $$(SF/2)+f(p)+f(SF)*SF,$$

wherein, SF is a skinfold measurement at a body location, (SF/2) being half the skinfold, f(p) is an adjustment for the pressure of compression during the measuring and is selected from a first range of about 0.1 to about 4 mm, and f(SF)*SF is an adjustment factor the skinfold measurement, where f(SF) is selected from a second range of about 0.01 to about 0.5, wherein the skinfold caliper outputs a needle injection length correlated to the determined depth of body fat.

* * * * *